(12) United States Patent
Brown et al.

(10) Patent No.: US 9,889,303 B2
(45) Date of Patent: Feb. 13, 2018

(54) FAR-FIELD R-WAVE DETECTION TO CONTROL ATRIAL PACE TIMING IN A DUAL-CHAMBER LEADLESS PACEMAKER

(71) Applicant: Medtronic, Inc., Minneapolis, MN (US)

(72) Inventors: Mark L. Brown, North Oaks, MN (US); Saul E. Greenhut, Aurora, CO (US); Troy E. Jackson, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 244 days.

(21) Appl. No.: 14/510,637

(22) Filed: Oct. 9, 2014

(65) Prior Publication Data

US 2016/0067486 A1 Mar. 10, 2016

Related U.S. Application Data

(60) Provisional application No. 62/047,391, filed on Sep. 8, 2014.

(51) Int. Cl.

| | |
|---|---|
| *A61N 1/00* | (2006.01) |
| *A61N 1/365* | (2006.01) |
| *A61N 1/368* | (2006.01) |
| *A61N 1/375* | (2006.01) |
| *A61B 5/0452* | (2006.01) |
| *A61N 1/372* | (2006.01) |

(Continued)

(52) U.S. Cl.
CPC .......... *A61N 1/365* (2013.01); *A61B 5/04012* (2013.01); *A61B 5/0428* (2013.01); *A61B 5/0452* (2013.01); *A61B 5/4836* (2013.01); *A61B 5/686* (2013.01); *A61N 1/368* (2013.01); *A61N 1/3756* (2013.01); *A61N 1/37205* (2013.01); *A61B 5/725* (2013.01); *A61B 5/7282* (2013.01); *A61N 1/371* (2013.01); *A61N 1/3704* (2013.01)

(58) Field of Classification Search
CPC ............................ A61N 1/365; A61B 5/04012
USPC ............................................. 607/17; 600/509
See application file for complete search history.

(56) References Cited

U.S. PATENT DOCUMENTS

| | | |
|---|---|---|
| 6,871,096 B2 | 3/2005 | Hill |
| 7,200,437 B1 | 4/2007 | Nabutovsky et al. |
| | (Continued) | |

OTHER PUBLICATIONS (PCT/US2015/042326) PCT Notification of Transmittal of the International Search Report and the Written Opinion of the International Searching Authority, dated Oct. 1, 2015, 11 pages.

*Primary Examiner* — Nadia A Mahmood

(57) ABSTRACT

A method for sensing far-field R-waves in a leadless, intracardiac pacemaker implanted in an atrium of a patient's heart may involve sensing an electrical signal generated by the heart with two electrodes and a first sensing channel and/or a second sensing channel of the pacemaker, comparing a first timing marker from the first sensing channel with a second timing marker from the second sensing channel, and either determining that the sensed signal is a P-wave, if the first and second timing markers indicate that the sensed signal was sensed by the first and second sensing channels within a predetermined threshold of time from one another, or determining that the sensed signal is a far-field R-wave, if the sensed signal is sensed by the second sensing channel and not sensed by the first sensing channel.

12 Claims, 6 Drawing Sheets

(51) Int. Cl.
*A61B 5/00* (2006.01)
*A61B 5/04* (2006.01)
*A61B 5/0428* (2006.01)
*A61N 1/37* (2006.01)

(56) References Cited

U.S. PATENT DOCUMENTS

| | | |
|---|---|---|
| 7,634,313 B1 | 12/2009 | Kroll et al. |
| 8,050,750 B2 | 11/2011 | Jackson |
| 2005/0107839 A1* | 5/2005 | Sanders ............. A61N 1/37264 607/32 |
| 2012/0172892 A1 | 7/2012 | Grubac et al. |
| 2013/0123872 A1 | 5/2013 | Bornzin et al. |
| 2013/0138006 A1* | 5/2013 | Bornzin ................ A61B 5/042 600/509 |
| 2013/0325081 A1* | 12/2013 | Karst ................ A61N 1/36592 607/25 |
| 2014/0100627 A1 | 4/2014 | Min |
| 2014/0121719 A1 | 5/2014 | Bonner et al. |
| 2014/0121720 A1 | 5/2014 | Bonner et al. |

* cited by examiner

FAR-FIELD R-WAVE DETECTION TO CONTROL ATRIAL PACE TIMING IN A DUAL-CHAMBER LEADLESS PACEMAKER

CROSS-REFERENCE TO RELATED APPLICATION

This application claims priority to U.S. Provisional Application Ser. No. 62/047,391, filed on Sep. 8, 2014 and entitled "FAR-FIELD R-WAVE DETECTION TO CONTROL ATRIAL PACE TIMING IN A DUAL-CHAMBER LEADLESS PACEMAKER," the content of which is incorporated by reference herein in its entirety.

TECHNOLOGICAL FIELD

This disclosure relates to cardiac pacing devices and methods. More specifically, the disclosure relates to techniques for detecting far-field R-waves using a leadless pacemaker device.

BACKGROUND

Leadless pacemakers are used to sense electrical activity and/or deliver therapeutic signals to the heart. For some patients, one atrial pacemaker may be used in one atrium of the heart. In other patients, multiple leadless pacemakers may be used in at least one atrium and at least one ventricle of the heart. Each leadless pacemaker device typically includes one or more electrodes on its outer housing to deliver therapeutic electrical signals and/or sense intrinsic depolarizations of the heart. Each leadless pacemaker may be positioned within a chamber of the heart and, in some examples, may be anchored to a wall of the heart via a fixation mechanism.

In some cases, a leadless pacemaker may need to sense depolarizations of one or more chambers of the heart other than the chamber in which it is implanted, in order to time pacing signals. In dual-chamber, leadless pacemaker systems, two or more pacemakers in two or more chambers of the heart must be able to pace the chambers in synchronous fashion. At the same time, sending timing signals from one leadless pacemaker in one chamber of the heart to another leadless pacemaker in another chamber of the heart, as well as receiving and processing the delivered signals with the receiving pacemaker(s), consumes large amounts of battery power, thus decreasing the useful life of the leadless pacemaker devices.

One depolarization signal that might be sensed by an atrial leadless pacemaker device is a far-field R-wave ("FFRW"), which indicates ventricular depolarization. It is challenging, however, for currently available atrial leadless pacemakers to sense FFRWs. One reason for this difficulty is that atrial leadless pacemakers are not configured to distinguish between atrial depolarization waveforms (P-waves) and FFRWs. Additionally, FFRWs are typically undersensed by the leadless atrial pacemakers, which are designed primarily to sense P-waves. Furthermore, detection of FFRWs from an atrial leadless pacemaker is more difficult than doing so with a standard dual-chamber pacemaker, because the atrial leadless pacemaker does not know the timing of true ventricular senses and paces.

Therefore, it would be desirable to have a pacemaker device that could effectively sense depolarizations of heart chambers other than the one in which it is implanted. More specifically, it would be advantageous to have a leadless, atrial pacemaker device that could sense FFRWs and distinguish them from P-waves. Such a leadless, atrial pacemaker could use this sensed information to time pacing pulses, without requiring signaling between leadless pacemakers in multiple chambers of the heart.

SUMMARY

A leadless atrial pacing device (or "atrial pacemaker" or "atrial device") of the present disclosure is configured for implantation within an atrium of a patient's heart. The atrial device may pace the atrium, sense intrinsic atrial electrical activity, and detect ventricular activation. The atrial device may be configured to detect ventricular activation by detecting ventricular electrical activity and/or mechanical contraction of the ventricles. The atrial device may control the timing of pacing pulses delivered to the atrium based on when ventricular activation is detected.

The atrial device may operate as the sole pacing device implanted in the heart in some examples. In other examples, the atrial device may operate along with a leadless ventricular pacing device (or "ventricular pacemaker" or "ventricular device") that is configured for implantation within a ventricle of the patient's heart. The ventricular device may be configured to sense intrinsic ventricular depolarizations and pace the ventricle. In some examples, the ventricular device may be programmed such that the ventricular device paces at a backup pacing rate (e.g., less than the atrial pacing rate) for situations in which atrial depolarization does not precipitate a ventricular depolarization, e.g., during AV block.

The combination of the atrial and ventricular devices may be referred to herein as a leadless pacing system (or "leadless pacemaker system"). Various embodiments and details of a leadless pacing system are described in detail in U.S. Patent Application Pub. No. 2014/0121720, titled "Leadless Pacemaker System," and filed Oct. 31, 2012, the full disclosure of which is hereby incorporated by reference. The atrial device of the present disclosure may operate reliably without modification (e.g., reprogramming) when the ventricular device has been added to the patient's heart to form a leadless pacing system. The atrial device may operate reliably even when the ventricular device is added because the atrial device controls atrial pacing timing based on sensed ventricular activation, independent on the origin of the sensed ventricular activation. Accordingly, the atrial device of the present disclosure may function in a variety of different scenarios without modification, e.g., as a stand-alone pacing device or implanted along with another pacing device.

The leadless pacing system may coordinate pacing of the heart based on sensed cardiac electrical and/or mechanical activity without establishment of a communication link between the atrial device and the ventricular device. In this manner, the atrial device and the ventricular device may operate independently from one another in the sense that operation of the atrial and ventricular devices may depend on sensed cardiac activity (electrical or mechanical) and may not need to rely on wired or wireless communication, unlike typical pacemakers, including pulse generators and electrical leads. Since the atrial device and the ventricular device do not rely on communication to coordinate pacing of the heart, the atrial and ventricular devices may save power that otherwise would be used to coordinate operation of the devices via communication.

In one aspect of the present disclosure, a method for sensing far-field R-waves in a leadless, intracardiac pacemaker implanted in an atrium of a patient's heart may first involve sensing an electrical signal generated by the heart with two electrodes and at least one of a first sensing channel of the pacemaker or a second sensing channel of the pacemaker, where the first sensing channel is configured to sense P-waves and reject far-field R-waves, and the second sensing channel is configured to sense both P-waves and far-field R-waves. The method may further involve comparing, with a processor in the pacemaker, a first timing marker from the first sensing channel with a second timing marker from the second sensing channel. Finally, the method may either: (1) determine, with the processor, that the sensed signal is a P-wave, if the first and second timing markers indicate that the sensed signal was sensed by the first and second sensing channels within a predetermined threshold of time from one another; or determine, with the processor, that the sensed signal is a far-field R-wave, if the sensed signal is sensed by the second sensing channel and not sensed by the first sensing channel.

In some embodiments, the method may further involve repeating the sensing, comparing and determining steps for multiple electrical signals generated by the heart. Some embodiments may also involve repeating the sensing, comparing and determining steps during multiple cardiac cycles of the heart. Optionally, such an embodiment may also involve calculating, with the processor in the pacemaker, a moving average of far-field R-wave intervals. The method may also optionally include delivering a pacing therapy by the pacemaker to the atrium of the heart, based at least in part on the moving average.

In some embodiments, the method is performed using a system including the pacemaker in the atrium and at least one additional leadless pacemaker implanted in a ventricle of the heart. In one embodiment, a first band-pass filter of the first sensing channel has a frequency range with a low end of approximately 10 Hz to approximately 40 Hz and a high end of greater than approximately 30 Hz (+/−5%) and a low sensitivity threshold of about 1 mV. A second band-pass filter of the second sensing channel has a frequency range with a low end of approximately 0.5 Hz to approximately 20 Hz and a high end of greater than approximately 20 Hz and a high sensitivity threshold of about 0.15 mV. In one embodiment, the predetermined threshold of time is about 50 milliseconds.

The method may further include setting a blanking period after sensing the electrical signal, to prevent waveforms from being detected multiple times. The method may also further include setting an atrial pace timer of the pacemaker.

In another aspect of the present disclosure, a non-transitory, computer-readable storage medium may store a set of instructions that cause a leadless, intracardiac pacemaker implanted in an atrium of a patient's heart to perform a method. The method may include any or all of the steps outlined above.

In another aspect of the present disclosure, an implantable leadless pacemaker device may include: a housing; at least one attachment member on the housing for attaching the pacemaker device to an inner wall of a heart; a first electrode; a second electrode; a first sensing channel in the housing, configured to sense P-waves and having a first band-pass filter with a frequency range with a low end of approximately 10 Hz to approximately 40 Hz and a high end of greater than approximately 30 Hz (+/−5%) and a low sensitivity threshold of about 1 mV; a second sensing channel in the housing, configured to sense far-field R-waves and P-waves and having a second band-pass filter with a frequency range with a low end of approximately 0.5 Hz to approximately 20 Hz and a high end of greater than approximately 20 Hz and a high sensitivity threshold of about 0.15 mV; and a processor configured to distinguish between P-waves and far-field R-waves based on data from the sensing channels and to generate a timing signal for timing atrial pacing therapy delivered by the pacemaker.

In one embodiment, the first and second electrodes are spaced at least 17 millimeters apart. In one embodiment, the device also includes an analog-to-digital converter configured to convert analog signals detected by the electrodes into digital signals for processing by the sensing channels. In some embodiments, the sensing channels may be located within the processor.

In another aspect of the present disclosure, an intracardiac pacemaker system may include an implantable, leadless, atrial pacemaker device and an implantable, leadless, ventricular pacemaker device. The atrial device may have any of the characteristics and features described above.

In another aspect of the present disclosure, an implantable leadless pacemaker device may include: a housing; at least one attachment member on the housing for attaching the pacemaker device to an inner wall of a heart; a first electrode; a second electrode; and a processor configured to process data sensed by the electrodes and converted to digital data to distinguish between P-waves and far-field R-waves. The processor may include a first sensing channel, configured to sense P-waves and having a first band-pass filter with a frequency range with a low end of approximately 10 Hz to approximately 40 Hz and a high end of greater than approximately 30 Hz (+/−5%) and a low sensitivity threshold of about 1 mV. The processor may further include a second sensing channel, configured to sense far-field R-waves and P-waves and having a second band-pass filter with a frequency range with a low end of approximately 0.5 Hz to approximately 20 Hz and a high end of greater than approximately 20 Hz and a high sensitivity threshold of about 0.15 mV.

These and other aspects and embodiments are described in greater detail below, in relation to the attached drawing figures.

DETAILED DESCRIPTION

Figure 1:
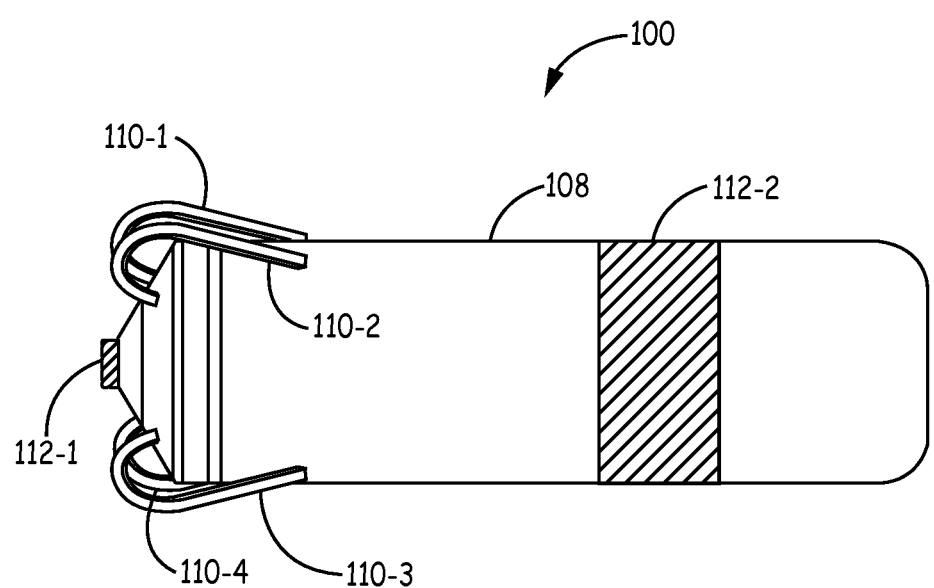
FIG. 1 shows an example leadless pacemaker device.

An implantable atrial pacemaker device of the present disclosure is configured for implantation within the atrium of a patient's heart. The atrial device may pace the atrium, sense intrinsic atrial electrical activity, and detect ventricular activation. The atrial device may control the timing of pacing pulses delivered to the atrium based on the detected ventricular activity.

The atrial device may include a hermetically sealed housing having a size and form factor that allows the atrial device to be implanted within the atrium. In some examples, the housing may have a cylindrical (e.g., pill-shaped) form factor. The housing may include fixation tines that connect the housing to the cardiac tissue within the atrium. The fixation tines may anchor the atrial device to the atrial cardiac tissue such that the atrial device moves along with the atrial cardiac tissue during cardiac contractions.

The housing of the atrial device may house components for sensing cardiac electrical activity such as intrinsic atrial depolarizations and ventricular depolarizations, e.g., far-field R-waves (FFRWs). The atrial device may also house components for delivering electrical stimulation therapy, such as pacing pulses. In some examples, the atrial device may also house components for sensing physiological parameters, such as acceleration, pressure, sound, and/or impedance.

The atrial device may include a plurality of electrodes used for sensing cardiac electrical activity and delivering electrical stimulation therapy (e.g., pacing pulses). For example, the atrial device may include a tip electrode and a ring electrode. The tip electrode may be located on the housing such that the tip electrode contacts the cardiac tissue when the atrial device is anchored to the cardiac tissue by the fixation tines. The ring electrode may also be located on the housing. For example, the ring electrode may be disposed around the circumference of the housing.

The atrial device may be configured to detect ventricular activation events. Ventricular activation may generally refer to electrical depolarization of the ventricular cardiac tissue and the subsequent mechanical contraction of the ventricular cardiac tissue. The atrial device may be configured to detect ventricular activation based on the detection of ventricular electrical activity and/or based on the detection of mechanical contraction of the ventricles. As used herein, detection of ventricular activation may generally refer to the detection of ventricular electrical activity (e.g., FFRWs) and/or the detection of mechanical contraction of the ventricles (e.g., based on heart sounds). In some examples, the atrial device may detect ventricular activation by detecting FFRWs. In some examples, the atrial device may detect ventricular activation by detecting S1 heart sounds. Although the atrial device may detect ventricular activation based on FFRWs and/or heart sounds, it is contemplated that the atrial device may detect ventricular activation using other sensors and techniques.

In some examples, the atrial device may detect FFRWs in the atrium, which are indicative of a ventricular depolarization. For example, the atrial device may detect FFRWs and determine when ventricular depolarization has occurred based on the detection of FFRWs. Although the atrial device is described herein as detecting ventricular depolarization based on the detection of FFRWs, the atrial device may also detect ventricular depolarization based on detected ventricular electrical activity other than FFRWs.

Additionally, or alternatively, the atrial device may be configured to detect mechanical contraction of the ventricles. For example, the atrial device may detect physiological parameters other than cardiac electrical activity, such as acceleration and/or pressure. In some examples, the atrial device may include one or more sensors that measure acceleration and/or pressure in the atrium. In these examples, the atrial device may detect mechanical contraction of the ventricles based on signals generated by the one or more sensors. For example, the atrial device may detect S1 heart sounds indicative of closure of the atrioventricular valves at the beginning of ventricular contraction and then determine that ventricular contraction has occurred based on the detection of S1 heart sounds. Additionally, or alternatively, the atrial device may detect S2 heart sounds in some examples, and then determine that ventricular contraction has occurred based on the detection of S2 heart sounds.

The atrial device may control atrial pacing timing based on when ventricular activation is detected during a cardiac cycle. In some examples, the atrial device may determine when to pace the atrium based on when FFRWs are detected during the cardiac cycle. Additionally, or alternatively, the atrial device may determine when to pace the atrium based on when S1 heart sounds are detected during the cardiac cycle. A cardiac cycle may refer to cardiac electrical activity that occurs from the beginning of one heartbeat to the beginning of the next heartbeat, as sensed by electrodes and/or sensors of the atrial device. Components of the atrial device that sense cardiac electrical activity, sense contraction of the ventricles, and control the delivery of electrical stimulation to the atrium are described hereinafter.

The atrial device may include an electrical sensing module (i.e., sensing module) that is configured to monitor cardiac electrical activity in the atrium. The sensing module may include electronic components that acquire cardiac electrical signals via the electrodes of the atrial device (e.g., the tip and ring electrodes). In some examples, the sensing module may implement signal conditioning on the acquired electrical signals. For example, the sensing module may filter, amplify, and digitize the acquired electrical signals. The electrical activity monitored by the sensing module may include a variety of different electrical signal components. The electrical activity may include intrinsic cardiac electrical activity, e.g., intrinsic atrial activity and/or intrinsic ventricular electrical activity, or other electrical signals.

The atrial device may include one or more sensors, such as an accelerometer and/or a pressure sensor. An accelerometer included in the atrial device may generate signals that indicate the acceleration of the atrial device. A pressure sensor included in the atrial device may generate signals that indicate pressure within the atrium. When the atrial device includes a pressure sensor or an accelerometer, the atrial device may detect ventricular activation based on signals generated by the sensors. For example, as described above, the atrial device may detect contraction of the ventricles based on sensor signals indicative of ventricular contraction, such as S1 heart sounds.

The atrial device may include a stimulation generator module (i.e., "stimulation generator") that is configured to deliver electrical stimulation to the atrium via the electrodes (e.g., the tip and ring electrodes). For example, the atrial device may deliver pacing pulses to the atrium via the electrodes. In some examples, the atrial device may deliver electrical stimulation other than pacing pulses, such as anti-tachycardia pacing (ATP) therapy.

The atrial device may include a processing module that receives sensing data from the sensing module. The data received from the sensing module may include digitized electrical activity that was received via the electrodes of the atrial device. The processing module may detect intrinsic atrial activity based on the sensing data received from the sensing module. For example, the processing module may detect an intrinsic atrial depolarization based on the sensing data received from the sensing module. Detection of intrinsic atrial depolarization by the processing module may be referred to as an "atrial sensed event" or a "sensed atrial event" in some examples. Atrial electrical activity that is precipitated by delivery of a pacing pulse from the stimulation generator may be referred to as an "atrial paced event."

The processing module may detect ventricular activation events in a variety of different ways. In some examples, the processing module may detect ventricular electrical activity (e.g., FFRWs). In some examples, the processing module may detect ventricular contraction based on signals received from the one or more sensors included in the atrial device. For example, the processing module may detect heart sounds (e.g., the S1 heart sound) based on the signals received from the one or more sensors and detect ventricular contractions based on the detected heart sounds. Heart sounds may be mechanical perturbations generated during contractions of the heart, such as blood flow and the closing of heart valves. The sensors (e.g., acceleration and/or pressure sensors) may generate signals in response to the mechanical perturbations. Heart sounds may be referred to as S1, S2, S3, or S4 heart sounds, for example. The S1 heart sound may be caused by closure of the atrioventricular valves, e.g., the tricuspid and/or mitral valves at the beginning of ventricular contraction. As such, the S1 heart sound may indicate ventricular contraction. The processing module may also detect heart sounds S2, S3, and S4 in some examples, and determine other cardiac parameters based on the detected heart sounds.

As described above, the processing module may detect ventricular activation based on the detection of ventricular electrical activity (e.g., FFRWs) and/or based on the detection of other ventricular contractions (e.g., S1 heart sounds). In some examples, the processing module may detect ventricular activation based only on detected ventricular electrical activity. In other examples, the processing module may detect ventricular activation based only on the detection of ventricular contractions, e.g., based only on accelerometer data and/or pressure data. In still other examples, the processing module may detect ventricular activation based on a combination of both ventricular electrical activity and detected ventricular contractions, e.g., both FFRWs and S1 heart sounds.

The processing module may control when the stimulation generator delivers pacing pulses (i.e., atrial pacing timing) based on when the processing module detects ventricular activation during a cardiac cycle. For example, the processing module may first determine an amount of time between a ventricular activation event and a previous atrial event (e.g., an intrinsic or paced atrial event) that preceded the detected ventricular activation event. Then, the processing module may schedule a time at which to deliver a pacing pulse to the atrium based on the determined amount of time between the ventricular activation event and the previous atrial event. The processing module may then control the signal generator module to deliver the pacing pulse to the atrium at the scheduled time. In some examples, the processing module may be configured to inhibit delivery of a pacing pulse at the scheduled time if the processing module senses an intrinsic atrial depolarization before the scheduled time at which the pacing pulse was to be delivered.

The processing module may control atrial pacing timing based on the detection of ventricular activation in a variety of different ways. The manner in which the processing module controls atrial pacing timing may depend on when ventricular activation occurs relative to the atrial event that preceded (e.g., precipitated) the ventricular activation. For example, the manner in which the processing module controls atrial pacing timing may depend on when a FFRW is sensed relative to the atrial event that preceded the FFRW.

As another example, the manner in which the processing module controls atrial pacing timing may depend on when an S1 heart sound is sensed relative to the atrial event that preceded the contraction causing the sensed S1 heart sound.

The atrial device of the present disclosure may operate as a stand-alone implantable device. In other words, the atrial device may operate as the sole pacing device implanted in the heart in some examples. Although the atrial device may operate as the sole pacing device implanted within the heart, in other examples, the atrial device may operate along with an implanted leadless ventricular pacemaker device. The ventricular device of the present disclosure may be implanted within a ventricle of the heart, sense ventricular depolarization, and pace the ventricle. The combination of the atrial and ventricular devices may be referred to herein as a leadless pacing system.

In some examples the atrial and ventricular devices may be implanted into the patient at the same time, e.g., during the same implant procedure. In other examples, the ventricular device may be implanted at a later time. For example, the patient may initially have the atrial device implanted to treat sick sinus syndrome (e.g., bradycardia), then have the ventricular device implanted at a later time after the patient develops AV block. In still other examples, the atrial device of the present disclosure may be implanted some time after the ventricular device has already been implanted in an earlier procedure. For example, the atrial device may be implanted after the ventricular device if the patient develops pacemaker syndrome subsequent to implantation of the ventricular pacing device.

The atrial device of the present disclosure may operate reliably without modification when a ventricular device has been added to the patient's heart to form a leadless pacing system. Put another way, the atrial device of the present disclosure may not require modification (e.g., reprogramming) in order to function along with a subsequently implanted ventricular device. The atrial device may operate even when the ventricular device is added because the atrial device controls atrial pacing timing based on sensed ventricular activation, independent on the origin of the sensed ventricular activation. For example, the atrial device may control pacing timing in the manner described herein whether the ventricular activation detected by the atrial device arises due to intrinsic ventricular depolarization or due to ventricular pacing by the ventricular device. Accordingly, the atrial device of the present disclosure may function in a variety of different circumstances without modification, e.g., as a stand-alone device or implanted along with another device.

Although the atrial device of the present disclosure may not require additional programming upon implantation of a ventricular device, in some examples, the ventricular device may be programmed to function along with the atrial device in order to provide more optimal cardiac pacing. Put another way, in some examples, the ventricular device may be configured (e.g., programmed) to operate along with the atrial device in order to assure that the leadless pacing system performs at an optimal level.

Figure 3:
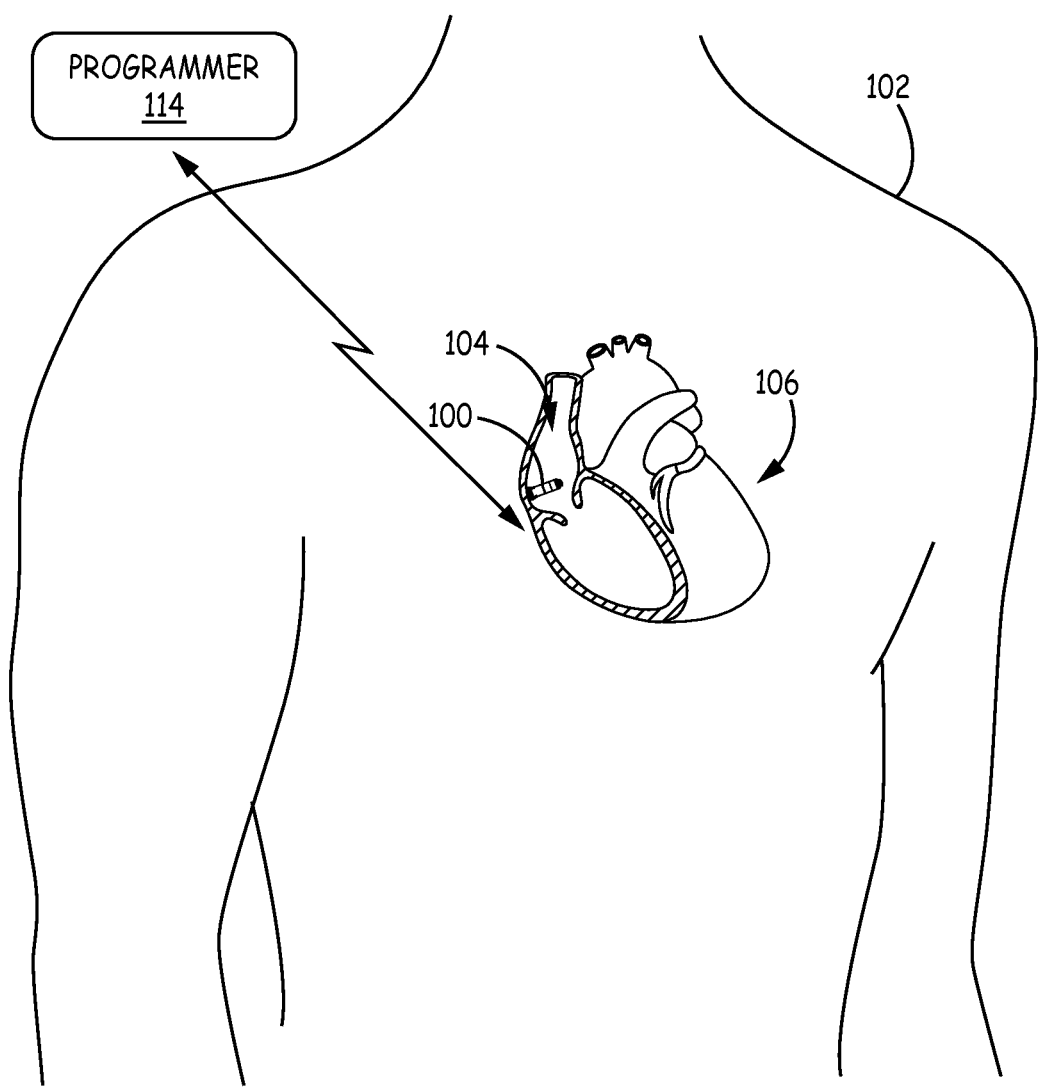
FIG. 3 shows an example leadless pacemaker device implanted in a patient that may be used to diagnose conditions of and provide therapy to a heart of the patient.

FIG. 1 shows a leadless atrial pacemaker device 100 (or "atrial device 100") that may be configured for implantation in a patient 102 (FIG. 3). For example, atrial device 100 may be configured for implantation within right atrium 104 of patient 102. Atrial device 100 may be configured to monitor electrical activity of heart 106 and/or provide electrical therapy to heart 106.

Atrial device 100 includes a housing 108, fixation tines 110-1, 110-2, 110-3, 110-4 (collectively "fixation tines 110"), and electrodes 112-1, 112-2. Housing 108 may have a pill-shaped cylindrical form factor in some examples. Fixation tines 110 are configured to connect (e.g., anchor) atrial device 100 to heart 106. Fixation tines 110 may be fabricated from a shape memory material, such as Nitinol. In some examples, fixation tines 110 may connect atrial device 100 to heart 106 within one of the chambers of heart 106. For example, as illustrated and described herein with respect to FIG. 3 and FIG. 11, fixation tines 110 may be configured to anchor atrial device 100 to heart 106 within right atrium 104. Although atrial device 100 includes a plurality of fixation tines 110 that are configured to anchor atrial device 100 to cardiac tissue in the right atrium, it is contemplated that a leadless device according to the present disclosure may be fixed to cardiac tissue in other chambers of a patient's heart using other types of fixation mechanisms.

Atrial device 100 may include one or more electrodes 112 for sensing electrical activity of heart 106 and/or delivering electrical stimulation to heart 106. Atrial device 100 includes two electrodes 112, although more than two electrodes may be included on an atrial device in other examples. Electrode 112-1 may referred to as "tip electrode 112-1." Electrode 112-2 may be referred to as a "ring electrode 112-2." Tip electrode 112-1 and ring electrode 112-2 may be spaced apart a sufficient distance to be able to detect various electrical signals generated by the heart, such as P-waves generated by atria and FFRWs generated by ventricles. In one embodiment, for example, electrodes 112-1, 112-2 may be spaced at least 17 mm apart from one another. Fixation tines 110 may anchor atrial device 100 to cardiac tissue such that tip electrode 112-1 maintains contact with the cardiac tissue. Ring electrode 112-2 may be located on housing 108. For example, ring electrode 112-2 may be a cylindrical electrode that wraps around housing 108. Although ring electrode 112-2 is illustrated as a cylindrical electrode that wraps around housing 108, ring electrode 112-2 may include other geometries. In some examples, housing 108 may be formed from a conductive material. In these examples, housing 108 may act as an electrode of atrial device 100.

Housing 108 houses electronic components of atrial device 100. Electronic components may include any discrete and/or integrated electronic circuit components that implement analog and/or digital circuits capable of producing the functions attributed to atrial device 100 described herein. For example, housing 108 may house electronic components that sense electrical activity via electrodes 112 and/or deliver electrical stimulation via electrodes 112. Additionally, housing 108 may also include memory that includes instructions that, when executed by one or more processing circuits housed within housing 108, cause atrial device 100 to perform various functions attributed to atrial device 100 herein. Housing 108 may also house sensors that sense physiological conditions of patient 102, such as an accelerometer and/or a pressure sensor.

In some examples, housing 108 may house a communication module that enables leadless device 100 to communicate with other electronic devices, such as programmer 114 or other external patient monitor. In some examples, housing 108 may house an antenna for wireless communication. Housing 108 may also include a power source, such as a battery. Electronic components included within housing are described in further detail hereinafter.

Figure 2:
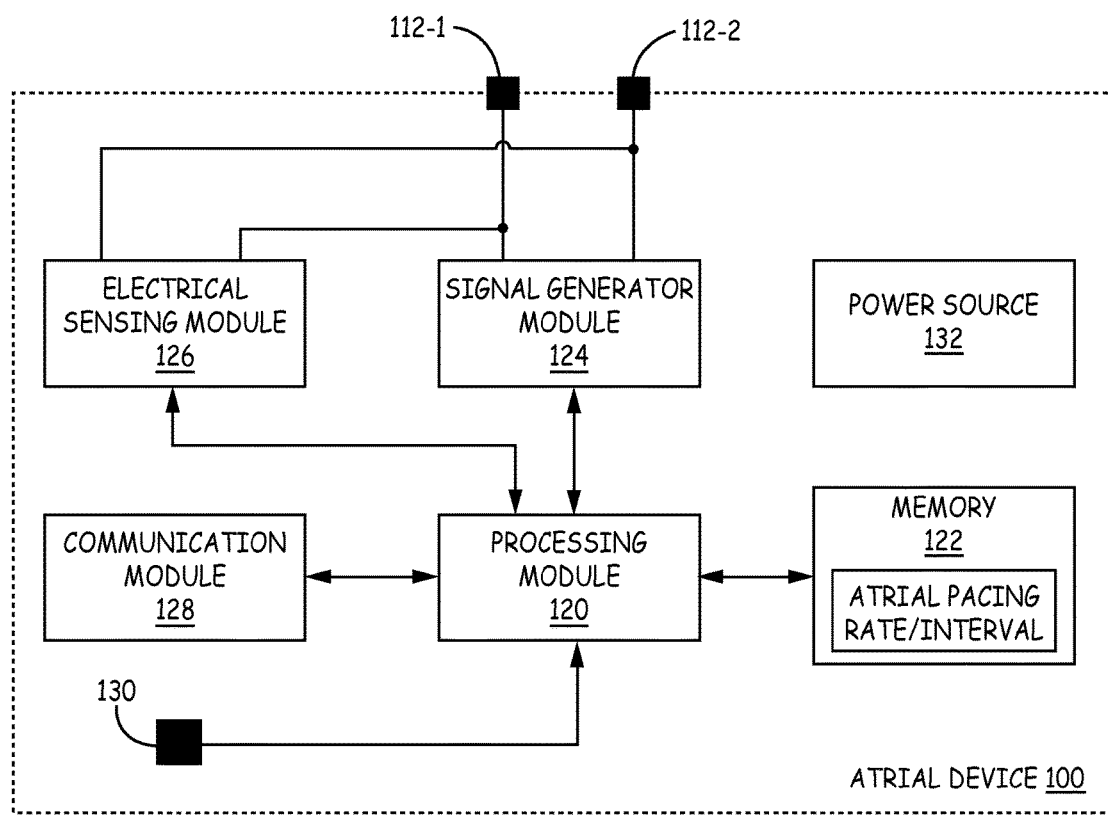
FIG. 2 is a functional block diagram of the example leadless pacemaker device.

FIG. 2 shows a functional block diagram of an example atrial device 100 configured for implantation within atrium 104 (FIG. 3). FIG. 3 shows a therapy system including atrial device 100 and programmer 114 that may be used to program atrial device 100 and retrieve data from atrial device 100. Atrial device 100 includes a processing module 120, memory 122, a signal generator module 124, an electrical sensing module 126, a communication module 128, a sensor 130, and a power source 132. Power source 132 may include a battery, e.g., a rechargeable or non-rechargeable battery.

Modules included in atrial device 100 represent functionality that may be included in atrial device 100 of the present disclosure. As discussed in U.S. Patent Application Pub. No. 2014/0121720, which was previously incorporated by reference, similar or identical modules and functionality may also be included in a ventricular pacemaker device, which may be provided as part of a dual-chamber, leadless pacemaker system for implantation and use in at least one atrium and at least one ventricle of a heart. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 120 may communicate with memory 122. Memory 122 may include computer-readable instructions that, when executed by processing module 120, cause processing module 120 to perform the various functions attributed to processing module 120 herein. Memory 122 may include any volatile, non-volatile, magnetic, or electrical media, such as RAM, ROM, NVRAM, EEPROM, Flash memory, or any other digital media. For example, memory 122 may include pacing instructions and values, such as the baseline atrial pacing rate, the baseline atrial pacing interval and the baseline AV interval. The pacing instructions and values may be updated by programmer 114 (FIG. 3). Pacing instructions included in memory 122 may cause atrial device 100 to operate as described in U.S. Patent Application Pub. No. 2014/0121720, which was previously incorporated by reference.

Processing module 120 may communicate with signal generator module 124 and electrical sensing module 126. Signal generator module 124 and electrical sensing module 126 are electrically coupled to electrodes 112. Electrical sensing module 126 is configured to monitor signals from electrodes 112 in order to monitor electrical activity of heart 106. Signal generator module 124 is configured to deliver electrical stimulation to atrium 104 via electrodes 112.

Processing module 120 may control signal generator module 124 to generate and deliver electrical stimulation to atrium 104 via electrodes 112. Electrical stimulation may include pacing pulses. In some examples, electrical stimulation may also include anti-tachycardia pacing (ATP) therapy. Processing module 120 may control signal generator module 124 to deliver electrical stimulation therapy according to one or more atrial therapy programs including pacing instructions and values, which may be stored in memory 122.

Electrical sensing module 126 may include circuits that acquire electrical signals. Electrical signals acquired by electrical sensing module 126 may include intrinsic cardiac electrical activity, such as intrinsic atrial and/or intrinsic ventricular cardiac electrical activity. Electrical sensing module 126 may filter, amplify, and digitize the acquired electrical signals to generate raw digital data. Processing module 120 may receive the digitized data generated by electrical sensing module 126. In some examples, processing module 120 may perform various digital signal processing operations on the raw data, such as digital filtering.

Processing module 120 may sense cardiac events based on the data received from electrical sensing module 126. For example, processing module 120 may sense atrial events based on the data received from electrical sensing module 126. In some examples, processing module 120 may sense ventricular activation based on the data received from electrical sensing module 126. For example, processing module 120 may detect FFRWs indicative of ventricular activation based on the data received from electrical sensing module 126.

In some embodiments, atrial pacemaker device 100 may be configured to sense ventricular events (e.g., FFRWs) and distinguish them from atrial depolarization events (e.g., P-waves). Such embodiments may include two or more sensing channels for doing so, and these channels may be part of sensing module 126 or processing module 120. Although the sensing channels are described below as being part of processing module 120, they may alternatively reside within sensing module 126 in other embodiments.

Figure 4:
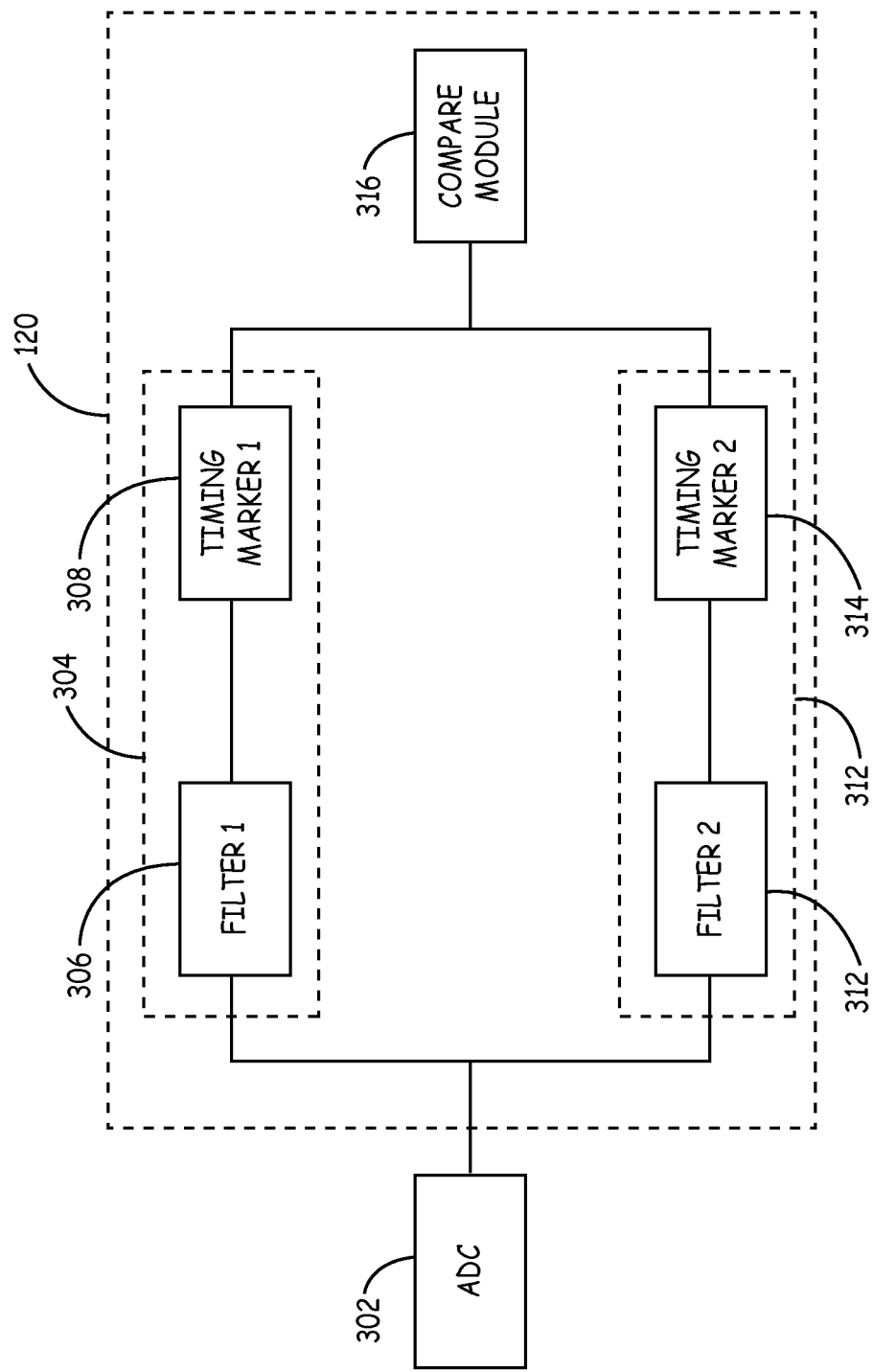
FIG. 4 is a functional block diagram of a portion of the example leadless pacemaker device, including a processing module and part of a sensing module.

Referring now to FIG. 4, in order to sense FFRWs and distinguish them from P-waves, atrial pacemaker device 100 may include two sensing channels in processing module 120—a first sensing channel 304 (or "P-wave sensing channel") configured to sense atrial depolarizations (e.g., P-waves) and reject (or "attenuate") FFRWs, and a second sensing channel 310 (or "P-wave and FFRW sensing channel") configured to sense P-waves and FFRWs. Digital signal data is fed to both channels 304, 310 from an analog-to-digital converter 302, which may be part of sensing module 126 (FIG. 2). In one embodiment, first sensing channel 304 may include a first band pass filter 306, with a range having a low end of approximately 10 Hz to approximately 40 Hz and a high end of greater than approximately 30 Hz and a low sensitivity threshold of about 1 mV. In one embodiment, for example, the range may be from about 20 Hz to about 610 Hz. Optionally, first filter 306 may be further tuned, for example by increasing the cutoff frequency, to better enable sensing of P-waves and rejection of FFRWs. First filter 306 may also include a relatively low sensitivity threshold, such as about 1 mV. First sensing channel 304 may further include a first timing marker module 308, configured to generate a timing marker and set a blanking period when an electrical signal passes through first filter 306. In one embodiment, for example, each blanking period may be approximately 100 milliseconds. Alternative embodiments may not include blanking periods.

For example, processing module 120 may be configured to count one sensed cardiac event within a predetermined time period and disregard any other events that are sensed within the predetermined time period.

Second sensing channel 310, which is configured to sense both P-waves and FFRWs, may include a second band-pass filter 312. In some embodiments, second band-pass filter 312 may have a range having a low end of approximately 0.5 Hz to approximately 20 Hz and a high end of greater than approximately 20 Hz, or more specifically in one embodiment a range of about 10-610 Hz. In an alternative embodiment, second filter 312 may have a range of about of 5-610 Hz. In any of these embodiments, second filter 312 may have a high sensitivity threshold, such as about 0.15 mV. Second filter 312 would thus tend to pass most of the P-wave and FFRW frequencies, resulting in sufficient P-wave and FFRW amplitude for sensing by the high sensitivity threshold. Second channel 310 may also include a second timing marker module 314, configured to generate a timing marker and set a blanking period when an electrical signal passes through first filter 312.

As just described, timing marker modules 308, 314 of processing module 120 may be configured to set timing markers whenever a signal in the predefined range is received by the filters 306, 312 in their respective sensing channels 304, 310 and to set a blanking period after each sensed event, to prevent waveforms from being sensed multiple times. Processing module 120 also includes a compare module 316, configured to compare timing markers from the two sense channels 304, 310. When a sense from first channel 304 occurs simultaneously or nearly simultaneously (e.g., within about 50 milliseconds) with a sense from second channel 310, compare module 316 labels the sense as a P-wave. When a sense from second channel 310 is not matched by a sense in first channel 304, compare module 316 labels the sense as a FFRW. A sense in first channel 304 not matched by a sense in second channel 310 should typically not occur, but may be labeled by compare module 316 a P-wave or noise by processing module 120. Processing module 120 may include criteria for designating a sensed event as either a P-Wave or noise. For example, the expected timing of a P-wave may be used to distinguish noise from an actual P-wave. If no sense occurs in either channel 304, 310, compare module 316 will classify this as "no sense."

Figure 5:
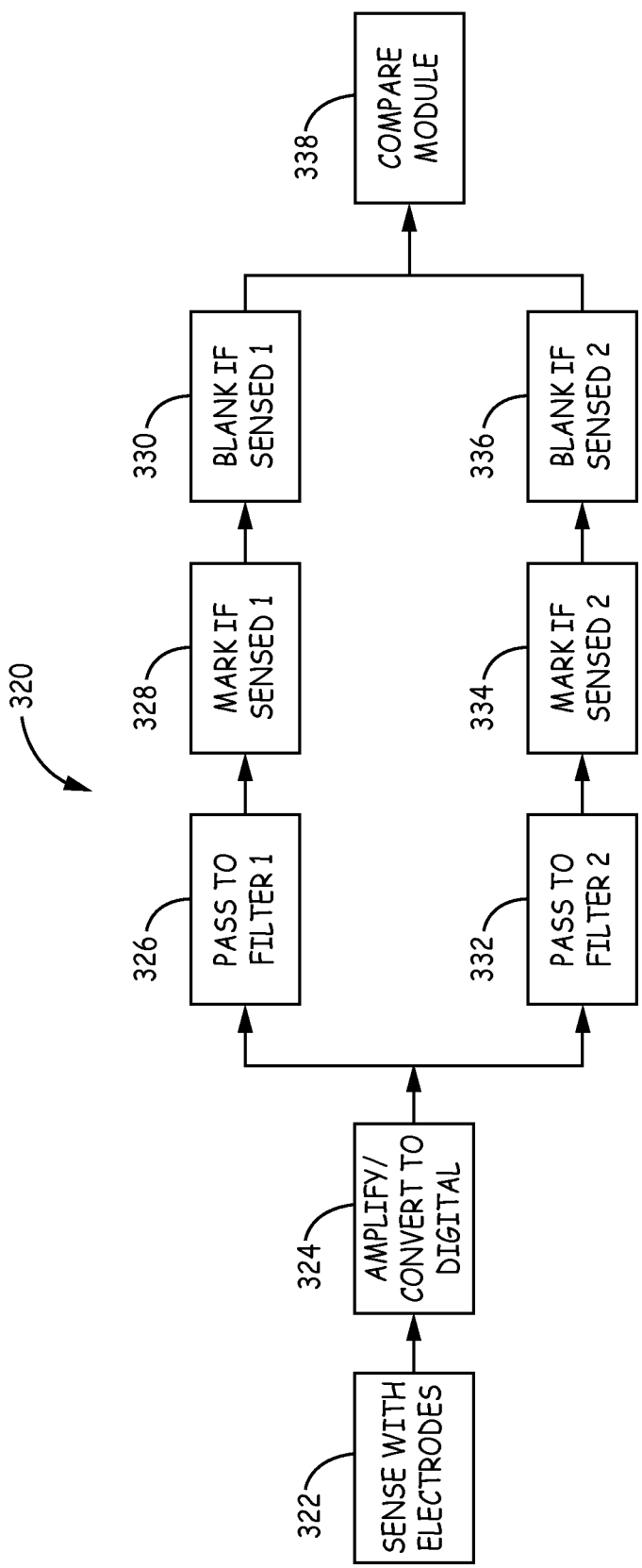
FIG. 5 is a flow diagram of a method for sensing far-field R-waves and distinguishing them from P-waves, according to one embodiment.

FIG. 5 illustrates a method 320 for sensing and distinguishing FFRWs and P-waves, according to one embodiment and using an atrial pacemaker device 100 such as that described above. In a first step, method 320 involves sensing an electrical signal of the heart 322 with two electrodes on atrial device 100. This sensed signal may then be amplified and converted into digital data 324, for example in the electrical sensing module 126 described above. The digitized signal is then passed to two filters, 326, 332. If the signal passes through a first filter 326, then a timing marker is set 328 by the first channel, and a blanking period is also set 330 by the first channel. If the signal passes through a second filter 332, then a timing marker is set 334 by the second channel, and a blanking period is also set 336 by the second channel. In a final step, method 320 involves comparing the timing markers 338 from the two sensing channels and labeling the signal as FFRW, P-wave, noise or "no sense," as described immediately above. The resulting atrial sense classification may then be sent to a timing algorithm of atrial device 100 to set a next atrial pace timer appropriately. (This step is not depicted in FIG. 5).

Figure 6:
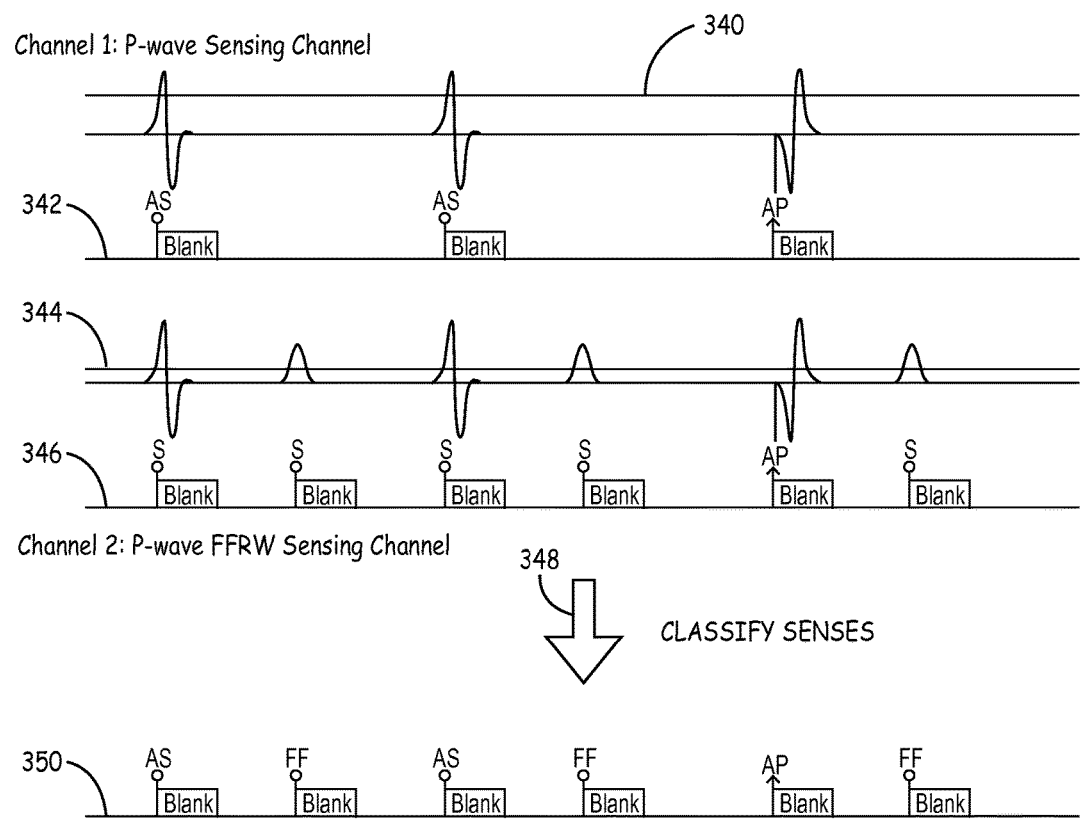
FIG. 6 is an electrocardiogram tracing and timing diagram, illustrating one example of timing of FFRW and P-wave sensing.

With reference now to FIG. 6, one example of sensing behavior of atrial leadless pacemaker 100 is illustrated. The topmost portion of FIG. 6 shows an ECG tracing 340 from first (P-wave) sensing channel 304, with three atrial events being illustrated as sensed. The line immediately below ECG tracing 340 is a timing line 342 for first sensing channel 304, illustrating two atrial sensed events and an atrial paced event, each followed by a blanking period.

The next portion of FIG. 6 is another ECG tracing 344, this one from second (P-wave and FFRW) sensing channel 310. Tracing 344 shows the same three atrial events as in the first channel tracing 340, but also illustrates three FFRWs, with three atrial events being illustrated as sensed. The line immediately below the ECG tracing 344 is a timing line 346 for second sensing channel 310, illustrating the P-waves and the additional three sensed events, with each of the events followed by a blanking period.

As discussed in reference to FIGS. 4 and 5, the sensed events are then classified 348 as P-waves or FFRWs. The final line 350 in FIG. 6 illustrates the classified events and blanking periods, according merely to one example.

Referring back to FIG. 2, sensor 130 may comprise at least one of a variety of different sensors. For example, sensor 130 may comprise at least one of a pressure sensor and an accelerometer. Sensor 130 may generate signals that indicate at least one of an activity level of patient 102, a hemodynamic pressure, and heart sounds. Processing module 120 may detect, for example, an activity level of patient 102, a hemodynamic pressure, and heart sounds based on the signals generated by sensor 130.

Communication module 128 may include any suitable hardware (e.g., an antenna), firmware, software, or any combination thereof for communicating with another device, such as programmer 114 or a patient monitor. Under the control of processing module 120, communication module 128 may receive downlink telemetry from and send uplink telemetry to other devices, such as programmer 114 (FIG. 3) or a patient monitor, with the aid of an antenna included in communication module 128. As described herein, a leadless pacing system may coordinate pacing of heart 106 based on sensed cardiac electrical and/or mechanical activity without establishment of a communication link between atrial device 100 and a ventricular device. Accordingly, communication module 128 is not required to include functionality that provides for communication between atrial device 100 and a ventricular device.

Programmer 114 may be a handheld computing device, desktop computing device, a networked computing device, etc. Programmer 114 may include a computer-readable storage medium having instructions that cause a processor of programmer 114 to provide the functions attributed to programmer 114 in the present disclosure. Atrial device 100 may wirelessly communicate with programmer 114. For example, atrial device 100 may transfer data to programmer 114 and may receive data from programmer 114. Programmer 114 may also wirelessly program and/or wirelessly charge atrial device 100.

Data retrieved from atrial device 100 using programmer 114 may include cardiac EGMs stored by atrial device 100 that indicate electrical activity of heart 106 and marker channel data that indicates the occurrence and timing of sensing, diagnosis, and therapy events associated with atrial device 100. Data transferred to atrial device 100 using programmer 114 may include, for example, operational programs for atrial device 100 that cause device 100 to operate as described herein.

As previously mentioned, atrial pacemaker device 100 may be combined in a system with one or more ventricular, leadless pacemaker devices. Such ventricular pacemaker devices may include any or all of the features described above in relation to atrial device 100 and may be implanted in a left ventricle, right ventricle, or both. Various embodiments and features dual-chamber, leadless pacing systems are described in detail in U.S. Patent Application Pub. No. 2014/0121720, which was previously incorporated by reference.

Various examples have been described. These and other examples are within the scope of the following claims.

The invention claimed is:

1. An implantable leadless pacemaker device, comprising:
 a housing;
 at least one attachment member on the housing for attaching the pacemaker device to an inner wall of a heart;
 only two electrodes, spaced far enough apart from one another to be able to detect P-waves generated by a chamber of the heart in which the pacemaker device is implanted and far-field R-waves in an adjacent chamber of the heart;
 a first sensing channel in the housing, configured to sense P-waves detected via the only two electrodes and having a first band-pass filter with a frequency range with a low end of approximately 10 Hz to approximately 40 Hz and a high end of greater than approximately 30 Hz and a low sensitivity threshold of about 1 mV;
 a second sensing channel in the housing, configured to sense far-field R-waves and P-waves detected via the only two electrodes and having a second band-pass filter with a frequency range with a low end of approximately 0.5 Hz to approximately 20 Hz and a high end of greater than approximately 20 Hz and a high sensitivity threshold of about 0.15 mV; and
 a processor configured to distinguish between P-waves and far-field R-waves based on a comparison between data from the first and second sensing channels and to generate a timing signal for timing atrial pacing therapy delivered by the pacemaker.

2. The device of claim 1, wherein the two electrodes are spaced at least 17 millimeters apart.

3. The device of claim 1, further comprising an analog-to-digital converter configured to convert analog signals detected by the electrodes into digital signals for processing by the sensing channels.

4. The device of claim 1, wherein the sensing channels are located within the processor.

5. An intracardiac pacemaker system, comprising:
 an implantable, leadless, ventricular pacemaker device; and
 an implantable, leadless, atrial pacemaker device, comprising:
 a housing;
 at least one attachment member on the housing for attaching the pacemaker device to an inner wall of a heart;
 only two electrodes, spaced far enough apart from one another to be able to detect P-waves generated by an atrium of the heart in which the pacemaker device is implanted and far-field R-waves in an adjacent ventricle of the heart;
 a first sensing channel in the housing, configured to sense P-waves detected via the only two electrodes and having a first band-pass filter with a frequency range with a low end of approximately 10 Hz to approximately 40 Hz and a high end of greater than approximately 30 Hz and a low sensitivity threshold of about 1 mV;

a second sensing channel in the housing, configured to sense far-field R-waves and P-waves detected via the only two electrodes and having a second band-pass filter with a frequency range with a low end of approximately 0.5 Hz to approximately 20 Hz and a high end of greater than approximately 20 Hz and a high sensitivity threshold of about 0.15 mV; and a processor configured to distinguish between P-waves and far-field R-waves based on a comparison between timing markers from the sensing channels and to generate a timing signal for timing atrial pacing therapy delivered by the pacemaker.

6. The system of claim 5, wherein the two electrodes are spaced at least 17 millimeters apart.

7. The system of claim 5, further comprising an analog-to-digital converter configured to convert analog signals detected by the electrodes into digital signals for processing by the sensing channels.

8. The system of claim 5, wherein the sensing channels are located within the processor.

9. An implantable leadless pacemaker device, comprising:

a housing;

at least one attachment member on the housing for attaching the pacemaker device to an inner wall of a heart;

only two electrodes, spaced far enough apart from one another to be able to detect P-waves generated by a chamber of the heart in which the pacemaker device is implanted and far-field R-waves in an adjacent chamber of the heart; and a processor configured to process data sensed by the two electrodes and convert to digital data to distinguish between P-waves and far-field R-waves, wherein the processor comprises:

a first sensing channel, configured to sense P-waves detected via the only two electrodes and having a first band-pass filter with a frequency range with a low end of approximately 10 Hz to approximately 40 Hz and a high end of greater than approximately 30 Hz and a low sensitivity threshold of about 1 mV; and a second sensing channel, configured to sense far-field R-waves and P-waves detected via the only two electrodes and having a second band-pass filter with a frequency range with a low end of approximately 0.5 Hz to approximately 20 Hz and a high end of greater than approximately 20 Hz and a high sensitivity threshold of about 0.15 mV, and wherein the processor is configured to distinguish between P-waves and far-field R-waves based on a comparison between digital data from the first and second sensing channels.

10. The device of claim 1, wherein the processor is configured to distinguish between P-waves and far-field R-waves based on a comparison between timing markers from the first and second sensing channels.

11. The device of claim 10, wherein the processor is configured to determine a sensed waveform corresponds to a P-wave on condition that a timing marker from the first sending channel is matched to a timing marker from the second sensing channel within a particular temporal interval.

12. The device of claim 10, wherein the processor is configured to determine a sensed waveform corresponds to a R-wave on condition that a timing marker from the second sensing channel is unmatched to a timing marker from the first sensing channel.

* * * * *